US012723102B2

(12) United States Patent
Moon et al.

(10) Patent No.: US 12,723,102 B2
(45) Date of Patent: Sep. 1, 2026

(54) **COMPOSITION FOR DIFFERENTIAL DIAGNOSIS OF *ACANTHAMOEBA KERATITIS* COMPRISING CHORISMATE MUTASE PROTEIN ANTIBODIES, AND *ACANTHAMOEBA KERATITIS* DIAGNOSIS KIT USING SAME**

(71) Applicant: UNIVERSITY-INDUSTRY COOPERATION GROUP OF KYUNG HEE UNIVERSITY, Yongin-si (KR)

(72) Inventors: Eun Kyung Moon, Seoul (KR); Hae Ahm Lee, Seoul (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 839 days.

(21) Appl. No.: 17/817,459

(22) Filed: Aug. 4, 2022

(65) Prior Publication Data

US 2023/0054756 A1 Feb. 23, 2023

Related U.S. Application Data

(63) Continuation of application No. PCT/KR2021/000727, filed on Jan. 19, 2021.

(30) Foreign Application Priority Data

Feb. 6, 2020 (KR) ........................ 10-2020-0014563

(51) Int. Cl.
*C07K 16/40* (2006.01)
*G01N 33/569* (2006.01)

(52) U.S. Cl.
CPC ........... *C07K 16/40* (2013.01); *G01N 33/569* (2013.01)

(58) Field of Classification Search
CPC ...................................................... C07K 16/40
See application file for complete search history.

(56) References Cited

FOREIGN PATENT DOCUMENTS

| | | | |
|---|---|---|---|
| CN | 107501404 | A | 12/2017 |
| KR | 10-2010-0044736 | A | 4/2010 |
| KR | 10-1308516 | B1 | 9/2013 |
| KR | 10-1521409 | B1 | 5/2015 |

OTHER PUBLICATIONS

Bowdish et al. 1991 (Yeast expression of a catalytic antibody with chorismite mutase activity; Journal of Biological Chemistry; 266(18): 11901-11908) (Year: 1991).*

Moon et al. 2018 (Comparison of Proteins Secreted into Extracellular Space of Pathogenic and Non-pathogenic Acanthamoeba castellanii; Korean J Prasitol 56(6): 553-558) (Year: 2018).*

Sela-Culang et al. 2013 (The structural basis of antibody-antigen recognition; Frontiers in Immunology 4(302):1-13) (Year: 2013).*

Lloyd et al. 2009 (Modelling the human immune response: performance of a 1011 human antibody repertoire against a broad panel of therapeutically relevant antigens. Protein Engineering, Design & Selection 22(3):159-168 (Year: 2009).*

Goel et al. 2004 (Plasticity within the Antigen Combining Site May Manifest as Molecular Mimicry in the Humoral Immune Response; The Journal of Immunology 173(12):7358-7367 (Year: 2004).*

Edwards et al. 2003 (The remarkable flexibility of the human antibody repertoire; isolation of over one thousand different antibodies to a single protein, BlyS. Journal of Molecular Biology 334:103-118). (Year: 2003).*

International Search Report and Written Opinion issued in connection with corresponding PCT Application No. PCT/KR2021/000727.

Moon, E.-K. et al. Comparison of Proteins Secreted into Extracellular Space of Pathogenic and Nonpathogenic Acanthamoeba castellanii. Korean J. Parasitol. 2018, vol. 56, No. 6, pp. 553-558. See abstract; and p. 557.

Korean Office Action issued in connection with Application No. 9-5-2021-013171002 dated Feb. 16, 2021.

NCBI Blast:Protein Sequence 1.

NCBI Blast:Protein Sequence 2.

* cited by examiner

*Primary Examiner* — Gary B Nickol
(74) *Attorney, Agent, or Firm* — Tarolli, Sundheim, Covell & Tummino LLP

(57) ABSTRACT

The present invention relates to: a composition for differentially diagnosing *Acanthamoeba* keratitis, the composition comprising chorismate mutase antibodies; and an *Acanthamoeba* keratitis diagnosis kit using same. The composition comprising chorismate mutase antibodies according to the present invention causes an antigen-antibody reaction only specific to a chorismate mutase protein secreted from *Acanthamoeba*, thus making it possible to diagnose *Acanthamoeba* keratitis and differentiate the cause of *Acanthamoeba* keratitis more rapidly and accurately than existing methods for diagnosing *acanthamoeba* keratitis. The composition is expected to be widely applicable to the production of *Acanthamoeba* keratitis diagnosis kits, therapeutic agents, contact lens disinfecting agents, and the like using the composition.

1 Claim, 8 Drawing Sheets

Figure 2A:
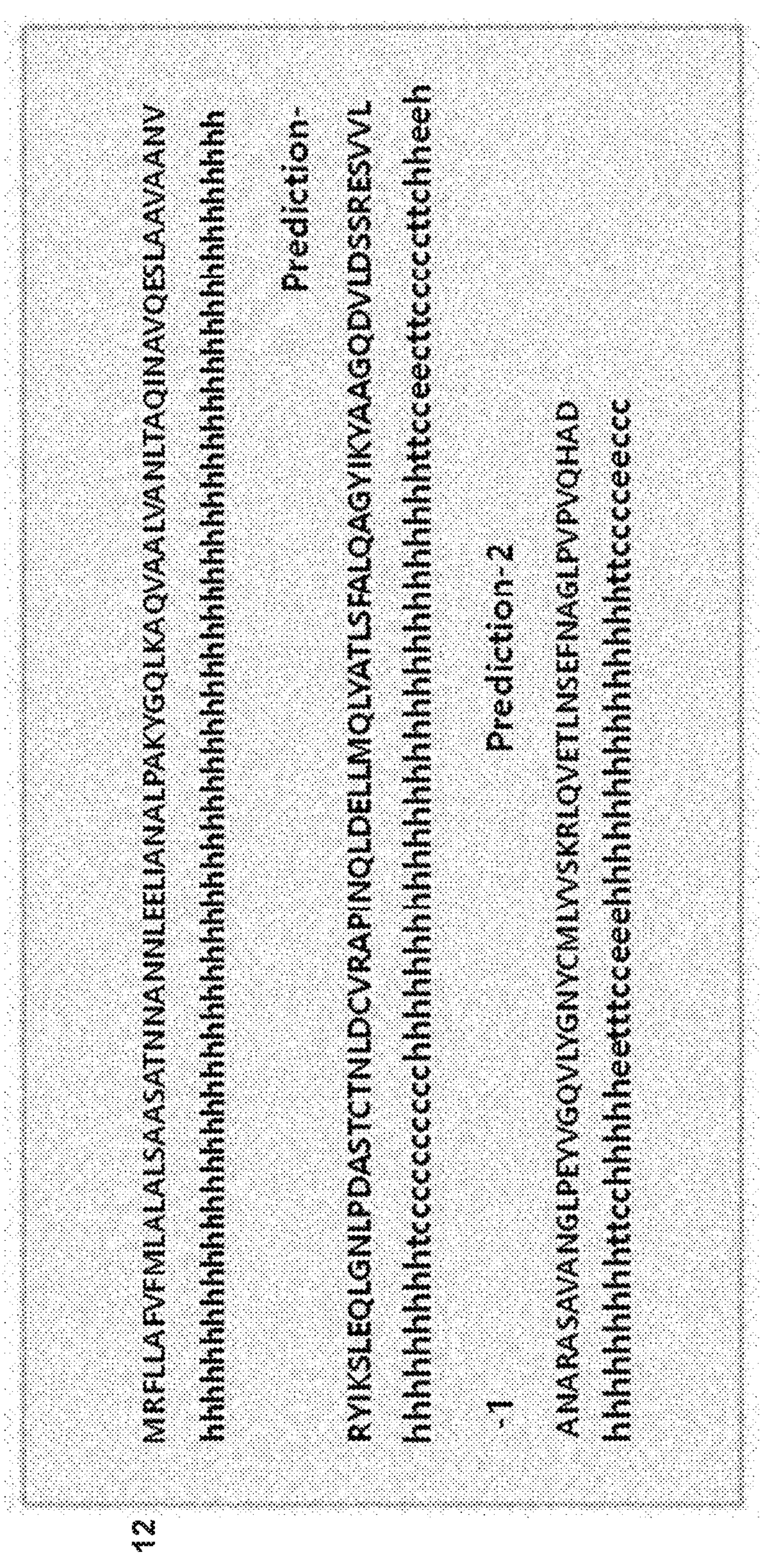

Specification includes a Sequence Listing.

【FIG. 1A】 SEQ. ID NO.: 11

ATGCGCTTCCTGCTCGCCTTCGTCTTCATGTTGGCTCTCGCCAGCGCGGCCTCGGCCACCAATAACGCCAACAACCTGGAGGAGCTGATCGCCAACGCCCTG
CCGGCCAAGTACGGCCAGCTCAAGGCCCAGGTGGCCGCCCTCCAGGCCAACCTCACGGCGCAGATCAACGCCGTCCAGGAGTCGCTCGCCGCGGTGGCGGCC
AACGTGCGCTACATCAAGTCGCTCGAGCAGCTGGGCAACCTGCCTGACGCCTCCACCTGCACCAACCTCGACTGCGTCCGCGCGCCCATCAACCAGCTCGAC
GAGCTCCTCATGCAGCTCTACGCCACGCGCCTCTCGTTCGCCCTCCAGGCCGGCTACATCAAGTACGCCGCGGGCCAGGACGTGCTGGACTCCAGCCGCGAG
TCGGTGGTGCTGGCCAACGCCCGCGCGAGCGCCGTCGCCAACGGCCTGCCCGAGTACGTGGGCCAGGTCCTCTACGGCAACTACTGCATGCTCTACGTCTCC
AAGCGCCTTCAGGTGGAGACCCTCAACTCCGAGTTCAACGCCGGCCTCCCCGTCCCCGTCCAGCACGCCGATTGA

【FIG. 1B】 SEQ. ID NO.: 12

MRFLLAFVFMLALASAASATNNANNLEELIANALPAKYGQLKAQVAALQANLTAQINAVQESLAAVAANVRYIKSLEQLGNLPDASTCTNLDCVRAPINQLD
ELLMQLYATRLSFALQAGYIKYAAGQDVLDSSRESVVLANARASAVANGLPEVVGQVLYGNYCMLYVSKRLQVETLNSEFNAGLFVPVQHAD

【FIG. 2B】
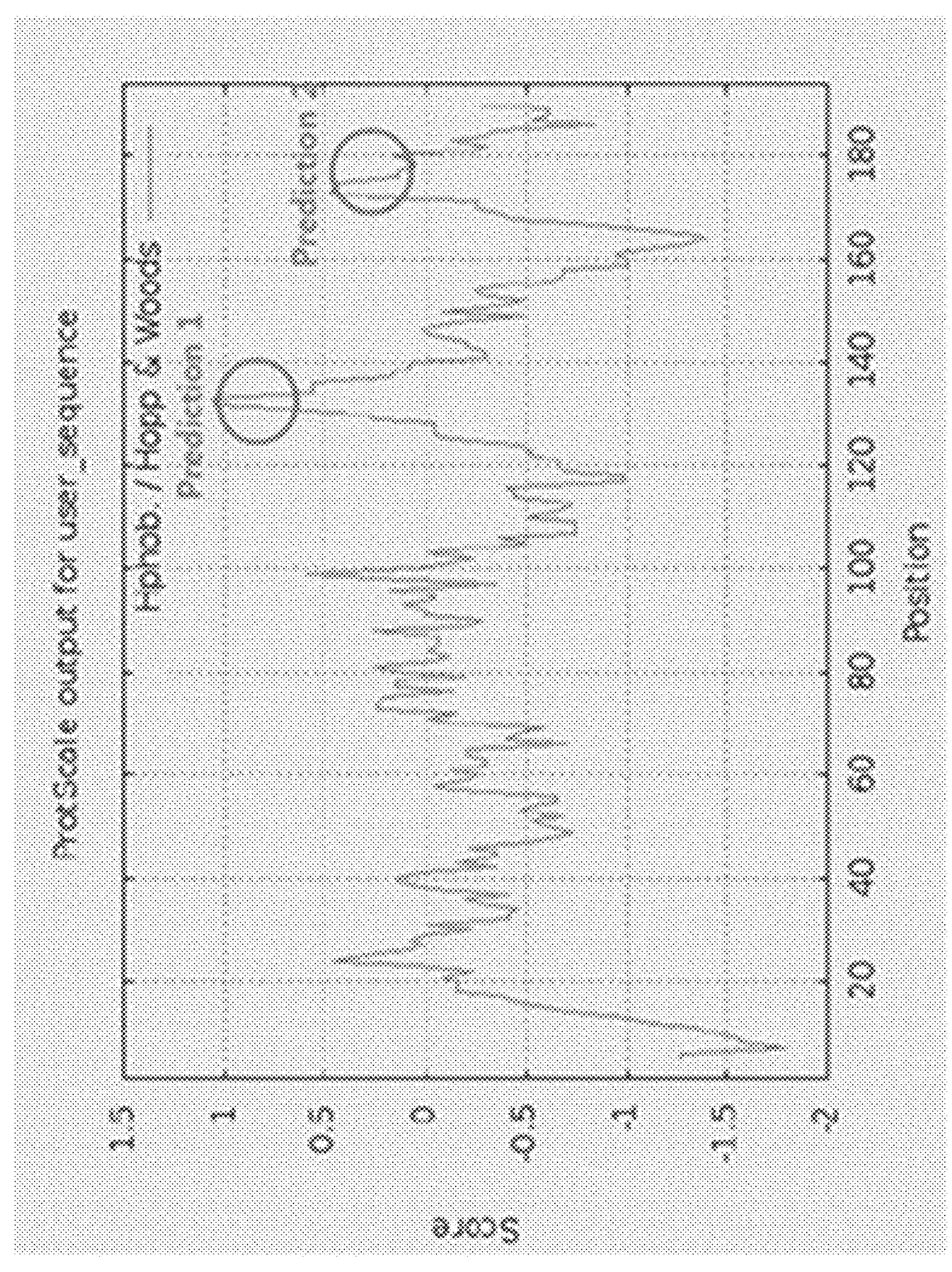

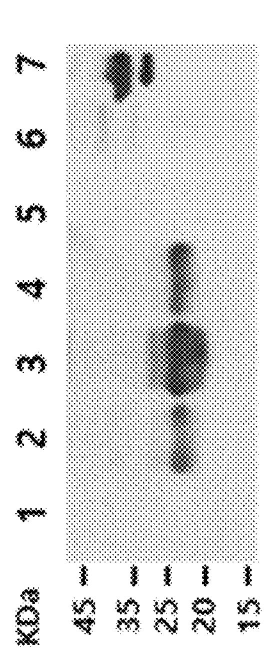
1. Human corneal epithelial cells
2. *Acanthamoeba castellanii* (#30011-nonpathogenic)
3. *Acanthamoeba castellanii* (#30868-pathogenic)
4. Clinical isolate (*Acanthamoeba* spp.)
5. *Fusarium solani*
6. *Pseudomonas aeruginosa*
7. *Staphylococcus aureus*

【FIG. 5】
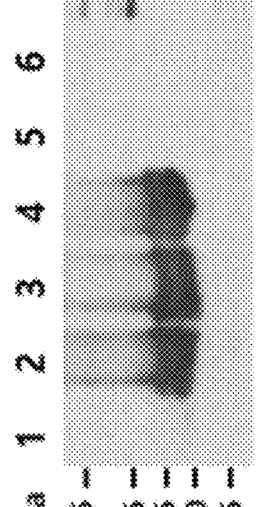
1. Human corneal epithelial cells
2. *Acanthamoeba castellanii* (#30011-nonpathogenic)
3. *Acanthamoeba castellanii* (#30868-pathogenic)
4. Clinical isolate (*Acanthamoeba* spp.)
5. *Fusarium solani*
6. *Pseudomonas aeruginosa*
7. *Staphylococcus aureus*

【FIG. 6】
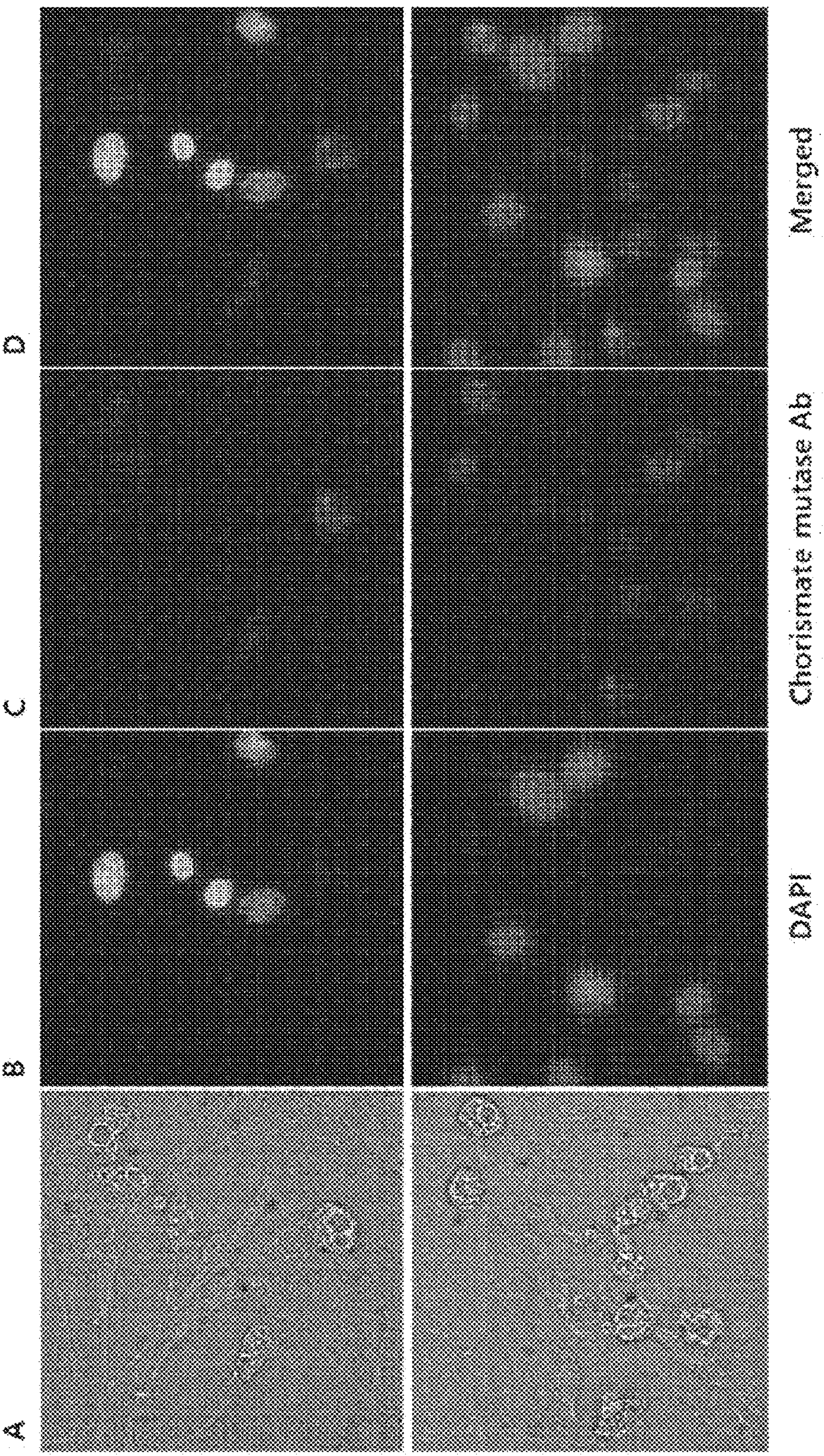

COMPOSITION FOR DIFFERENTIAL DIAGNOSIS OF *ACANTHAMOEBA KERATITIS* COMPRISING CHORISMATE MUTASE PROTEIN ANTIBODIES, AND *ACANTHAMOEBA KERATITIS* DIAGNOSIS KIT USING SAME

RELATED APPLICATIONS

The present invention is a U.S. Bypass Continuation Patent Application, claiming priority to Serial No. PCT/KR2021/000727, filed on Jan. 19, 2021, which claims priority from Korean Patent Application No. 10-2020-0014563 filed on Feb. 6, 2020; the entireties of both are hereby incorporated herein by reference.

SEQUENCE LISTING

The instant application contains a Sequence Listing which has been submitted electronically in .xml format and is hereby incorporated by reference in its entirety. Said copy, created on Mar. 23, 2026, is named P022-014-US_xml_seq_revised.xml and is 20,900 bytes in size.

TECHNICAL FIELD

The present invention relates to: a composition for differentially diagnosing *Acanthamoeba* keratitis, the composition comprising chorismate mutase antibodies; and an *Acanthamoeba* keratitis diagnosis kit using the same.

BACKGROUND ART

The cornea is the outermost surface of the eyeball, which occupies about 1/6 of the outer membrane of the eyeball and is one of the main membranes that refract light, is characterized in that light first passes through the eye and there are no blood vessels, and histologically, the corneal epithelium composed of 5 and 6 cell layers is classified into 6 layers including the Bowman's layer that is composed of cell-free collagen fibers, the corneal stroma that accounts for 90% of the thickness of the cornea, the Dua's layer, the Descemet's membrane composed of 3 and 4 layers of cells, and the corneal endothelium has a definite number of cells and extremely limited regeneration.

Due to its location at the front of the eye, the cornea may be heavily damaged by trauma, infection and other immune responses, and as a result, since the characteristics of the transparent cornea are lost, opacity remains, or new blood vessels and the like are formed, which may lead to serious loss of vision. Examples of the most common corneal diseases include corneal abrasions, corneal dystrophy, corneal ulcers, corneal neovascularization, Fuchs' dystrophy, keratitis, keratoconus, and the like, and keratitis, which causes inflammation of the cornea, accounts for 90% or more of corneal diseases.

Human keratitis is a disease in which bacteria or viruses invade the cornea to cause inflammation, and may be caused by *Staphylococcus* spp., *Pseudomonas* spp., *Fusarium* spp., *Acanthamoeba* spp., and the like, and after inflammation occurs, when the inflammation is not properly treated, the inflammation may cause painful ulcers and in severe cases, perforation of the eye may occur, or this may also lead to blindness. To prevent these symptoms, it is important to find the cause of keratitis at an early stage. Among the keratitis, keratitis due to *Acanthamoeba* infection shows symptoms such as red eye, excessive tear formation, foreign body sensation, and induction of pain when exposed to light, and although keratitis usually occurs in people who wear contact lenses, it is not easy to make a differential diagnosis from keratitis caused by bacteria and fungi.

Diagnosis of amoebic keratitis is made by collecting a tissue sample from the cornea of a patient with keratitis, and as a current diagnostic method, since the diagnosis is performed by a method such as microscopic observation or PCR, tissue needs to be cultured for a definitive diagnosis, so a diagnosis time of about one week is required. For this reason, early diagnosis is difficult and the treatment time is also extended. Therefore, there is an urgent need for a novel method for differentially diagnosing *Acanthamoeba* keratitis for rapid early treatment.

Meanwhile, although a primer set for detecting *Acanthamoeba* and a method for detecting keratitis-inducing *Acanthamoeba* using the same (Korean Patent No. 10-1308516) and the like have been researched, this is just a method for detecting *Acanthamoeba* using a primer set, and there is no technique for differentially diagnosing *Acanthamoeba* keratitis using an antibody against a specific protein secreted from *Acanthamoeba.* preferably 90% or more, and most preferably 95%, 96%, 97%, 98%, 99% or more with SEQ ID NO: 1.

As another exemplary embodiment of the present invention, the antibody according to the present invention may specifically bind to an amino acid site of highly antigenic SEQ ID NO: 2 consisting of a random coil portion confirmed by secondary structural analysis in a chorismate mutase protein, and may specifically bind to a site consisting of an amino acid sequence having a sequence homology of 70% or more, preferably 80% or more, more preferably 90% or more, and most preferably 95%, 96%, 97%, 98%, 99% or more with SEQ ID NO: 2.

The present inventors confirmed the effectiveness for the differentiation and diagnosis of a patient with keratitis using a composition including an antibody specific to the chorismate mutase protein.

In an exemplary embodiment of the present invention, as a result of performing western blot on cell cultures of human corneal epithelial (HCE) cells, non-pathogenic *Acanthamoeba* (*Acanthamoeba* castellanii #30011-nonpathogenic), pathogenic *Acanthamoeba* (*Acanthamoeba* castellanii #30868-pathogenic), a clinical isolate (Acanthamoebas spp.), *F. solani, P. aeruginosa* and *S. aureus*, it was confirmed that chorismate mutase was specifically detected only in *Acanthamoeba* (see Example 3), and further, as a result of performing western blot by obtaining the culture solution of each sample used in Example 3, it was confirmed that chorismate mutase was specifically detected only in *Acanthamoeba* (see Example 4).

Through the results, it was confirmed that a composition including the chorismate mutase antibody of the present invention could be usefully used for differential diagnosis of keratitis of a patient with *Acanthamoeba* keratitis.

As another aspect of the present invention, the present invention provides a kit for differentially diagnosing *Acanthamoeba* keratitis, including the composition.

As an exemplary embodiment of the present invention, the kit for differentially diagnosing *Acanthamoeba* keratitis may consist of one or more other constituent compositions, solutions or devices suitable for the analytical method.

As still another aspect of the present invention, the present invention provides a method for providing information for differentially diagnosing keratitis of a patient with *Acanthamoeba* keratitis, the method including: measuring an antigen-antibody reaction of an antibody specific to a chorismate mutase protein for a subject-derived biological sample.

As used herein, the term "method for providing information for differentially diagnosing keratitis of a patient with keratitis" means to provide objective information necessary for diagnosing a keratitis disease as a diagnosis or differentiation step, and excludes the physician's clinical judgment or findings. The subject-derived biological sample is not limited to, but may be, for example, a tissue, a cell, and the like, and is preferably a tissue or a cell derived from a patient with keratitis.

As yet another aspect of the present invention, the present invention provides a use of an antibody specific to a chorismate mutase protein for preparing a composition for differentially diagnosing *Acanthamoeba* keratitis.

Hereinafter, the present invention will be described in more detail through Examples. These Examples are only for exemplifying the present invention, and it will be apparent to those of ordinary skill in the art that the scope of the present invention is not to be construed as being limited by these Examples.

EXAMPLES

Example 1. Obtaining Chorismate Mutase from Proteins Secreted from *Acanthamoeba*

Obtaining Chorismate Mutase ORF

By obtaining the ORF of chorismate mutase among secreted proteins of pathogenic *Acanthamoeba* (ATCC #30868), 585 bp nucleotides of chorismate mutase, as illustrated in FIG. 1A, and 194 amino acids of chorismate mutase, as illustrated in FIG. 1B, were confirmed.

Analysis of secondary structure of chorismate mutase and confirmation of antigenicity of chorismate mutase As a result of analyzing the secondary structure of and confirming the antigenicity of the chorismate mutase protein obtained in Example 1-1, the secondary structure was analyzed as illustrated in FIG. 2A, and two highly antigenic portions Prediction 1 (GQDVLDSSRESVVLANAR) and Prediction 2 (RLQVETLNSEFNAGLPVPVQHAD) were confirmed as illustrated in FIG. 2B.

Figure 3:
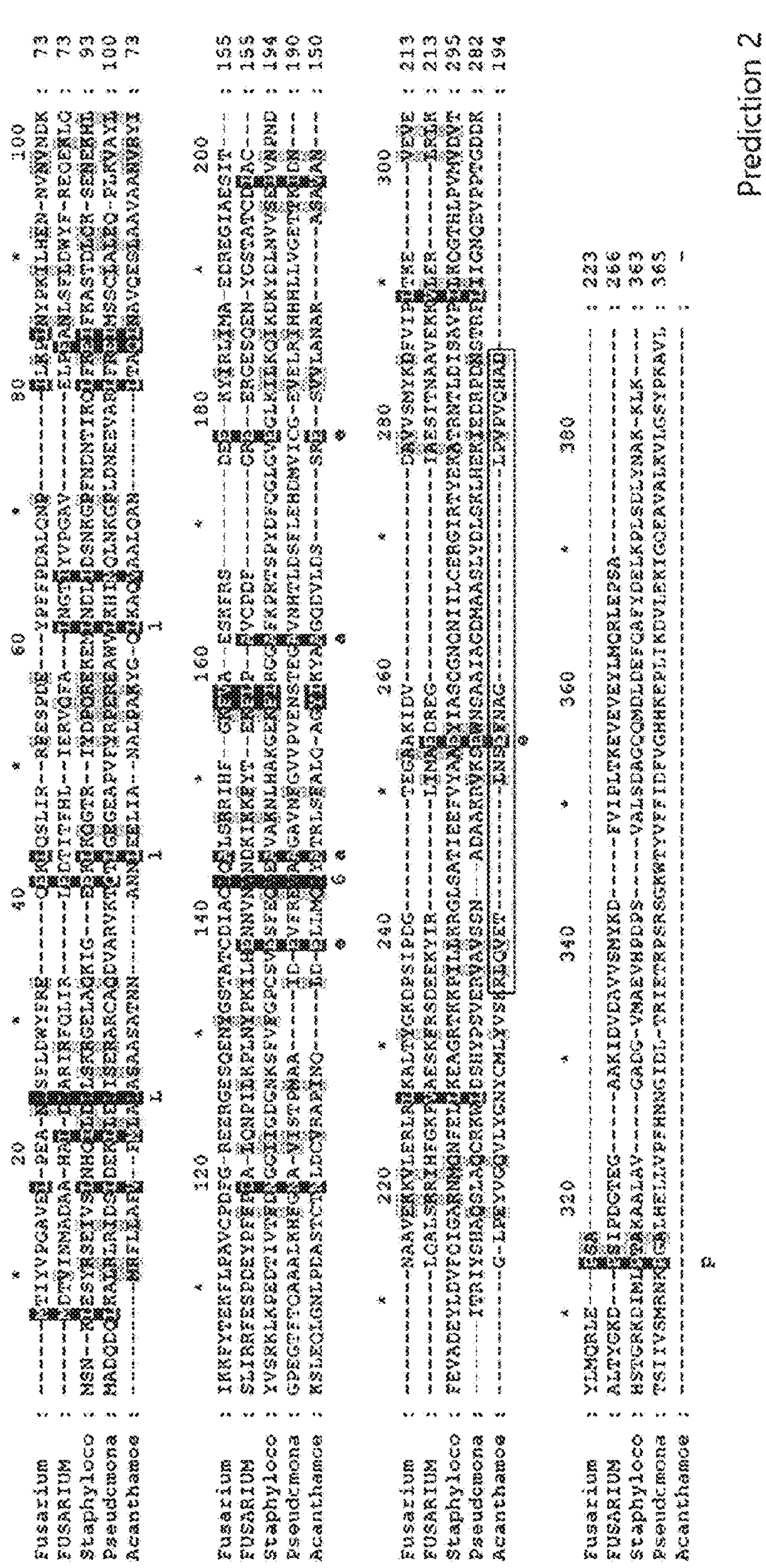

Example 2. Comparison of Antigenicity of Chorismate Mutase in Causative Bacteria and Fungi of Keratitis As a result of comparing the similarity between the highly antigenic portions (Prediction 1 and Prediction 2) derived in Example 1-2 and chorismate mutases of *Fusarium oxysprum* (1 and 2), *Staphylococcus aureus*, and *Pseudomonas aeruginosa*, which may be the cause of keratitis, as illustrated in FIG. 3, the results of exhibiting the difference of chorismate mutase were derived, and a relatively highly antigenic portion Prediction 2 (RLQVETLNSEFNAGLPVPVQHAD) was selected as an antibody-binding site.

Example 3. Confirmation of Detection of Chorismate Mutase Proteins in Cell Lysates As a result of obtaining an antibody specifically binding to the protein-antibody binding site of *Acanthamoeba* chorismate mutase selected in Example 2 by a known method and performing western blot on cell lysates of human corneal epithelial (HCE) cells, non-pathogenic *Acanthamoeba* (*Acanthamoeba* castellanii #30011-nonpathogenic), pathogenic *Acanthamoeba* (*Acanthamoeba* castellanii #30868-pathogenic), a clinical isolate (Acanthamoebas spp.), *F. solani, P. aeruginosa* and *S. aureus*, as illustrated in FIG. 4, it was confirmed that chorismate mutase was specifically detected only in *Acanthamoeba* cell lysates (2, 3 and 4 lines).

Example 4. Confirmation of Detection of Chorismate Mutase Proteins in Cell Culture Solution As a result of obtaining an antibody specifically binding to the protein-antibody binding site of *Acanthamoeba* chorismate mutase selected in Example 2 by a known method and performing western blot in cell culture solutions of human corneal epithelial (HCE) cells, non-pathogenic *Acanthamoeba* (*Acanthamoeba* castellanii #30011-nonpathogenic), pathogenic *Acanthamoeba* (*Acanthamoeba* castellanii #30868-pathogenic), a clinical isolate (*Acanthamoeba* spp.), *F. solani, P. aeruginosa* and *S. aureus*, as illustrated in FIG. 5, it was confirmed that chorismate mutase was specifically detected only in *Acanthamoeba* cell culture solutions (2, 3 and 4 lines).

From the results, it could be confirmed that the antibody of the present invention specifically binds only to *Acanthamoeba.*

Example 5. Confirmation of Detection of *Acanthamoeba* in Corneal Cells Infected with *Acanthamoeba*

After human corneal epithelial (HCE) cells were infected with *Acanthamoeba* (*Acanthamoeba* castellanii #30868-pathogenic), the presence of cells was confirmed by staining the infected cells with 4',6-diamidino-2-phenylindole (DAPI) (B of FIG. 6), and the cells were reacted with an antibody specifically binding to a protein-antibody binding site of *Acanthamoeba* chorismate mutase selected in Example 2.

As a result, as illustrated in C of FIG. 6, it was confirmed that only *Acanthamoeba* was specifically detected.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

INDUSTRIAL APPLICABILITY

The composition of the present invention can cause an antigen-antibody reaction only specific to chorismate mutase secreted from *Acanthamoeba*, thus making it possible to diagnose *Acanthamoeba* keratitis and differentiate the cause of *Acanthamoeba* keratitis more rapidly and accurately than existing methods for diagnosing *Acanthamoeba* keratitis. The composition is expected to be widely applicable to the production of *Acanthamoeba* keratitis diagnosis kits, therapeutic agents, contact lens disinfecting agents, and the like.

SEQUENCE LISTING

```
Sequence total quantity: 15
SEQ ID NO: 1           moltype = AA  length = 194
FEATURE                Location/Qualifiers
source                 1..194
                       mol_type = protein
                       note = Chorismate mutase peptide (FIG 1B, 2A, 3)
                       organism = Acanthamoeba castellanii
SEQUENCE: 1
MRFLLAFVFM LALASAASAT NNANNLEELI ANALPAKYGQ LKAQVAALQA NLTAQINAVQ  60
ESLAAVAANV RYIKSLEQLG NLPDASTCTN LDCVRAPINQ LDELLMQLYA TRLSFALQAG  120
YIKYAAGQDV LDSSRESVVL ANARASAVAN GLPEYVGQVL YGNYCMLYVS KRLQVETLNS  180
EFNAGLPVPV QHAD                                                    194

SEQ ID NO: 2           moltype = AA  length = 23
FEATURE                Location/Qualifiers
source                 1..23
                       mol_type = protein
                       note = Chorismate mutase peptide prediction 2
                       organism = synthetic construct
SEQUENCE: 2
RLQVETLNSE FNAGLPVPVQ HAD                                          23

SEQ ID NO: 3           moltype = AA  length = 5
FEATURE                Location/Qualifiers
REGION                 1..5
                       note = Chorismate mutase antibody VH CDR1
source                 1..5
                       mol_type = protein
                       organism = synthetic construct
SEQUENCE: 3
SGYWN                                                              5

SEQ ID NO: 4           moltype = AA  length = 16
FEATURE                Location/Qualifiers
REGION                 1..16
                       note = Chorismate mutase antibody VH CDR2
source                 1..16
                       mol_type = protein
                       organism = synthetic construct
SEQUENCE: 4
YINYSGRTYY NPSLKS                                                  16

SEQ ID NO: 5           moltype = AA  length = 6
FEATURE                Location/Qualifiers
REGION                 1..6
                       note = Chorismate mutase antibody VH CDR3
source                 1..6
                       mol_type = protein
                       organism = synthetic construct
SEQUENCE: 5
GYDEAY                                                             6

SEQ ID NO: 6           moltype = AA  length = 114
FEATURE                Location/Qualifiers
REGION                 1..114
                       note = Chorismate mutase antibody VH
source                 1..114
                       mol_type = protein
                       organism = synthetic construct
SEQUENCE: 6
EVQVQESGPS LVKPSQTLSL TCSVTGDSIT SGYWNWIRKF PGNKLEYMGY INYSGRTYYN  60
PSLKSRISIT RDTSKNQCYL QLNSVTTEDT ATYYCAGGYD EAYWGQGTLV TVSA        114

SEQ ID NO: 7           moltype = AA  length = 11
FEATURE                Location/Qualifiers
REGION                 1..11
                       note = Chorismate mutase antibody LH CDR1
source                 1..11
                       mol_type = protein
                       organism = synthetic construct
SEQUENCE: 7
RASKSISKYL A                                                       11

SEQ ID NO: 8           moltype = AA  length = 7
FEATURE                Location/Qualifiers
REGION                 1..7
                       note = Chorismate mutase antibody LH CDR2
source                 1..7
```

-continued

```
                        mol_type = protein
                        organism = synthetic construct
SEQUENCE: 8
SGSNLKS                                                                7

SEQ ID NO: 9            moltype = AA  length = 9
FEATURE                 Location/Qualifiers
REGION                  1..9
                        note = Chorismate mutase antibody LH CDR3
source                  1..9
                        mol_type = protein
                        organism = synthetic construct
SEQUENCE: 9
QQHNEYPWT                                                              9

SEQ ID NO: 10           moltype = AA  length = 107
FEATURE                 Location/Qualifiers
REGION                  1..107
                        note = Chorismate mutase antibody LH
source                  1..107
                        mol_type = protein
                        organism = synthetic construct
SEQUENCE: 10
DVQITQSPSY LAASPGETIT INCRASKSIS KYLAWYQEKP GKTNKLLIYS GSNLKSGIPS  60
RFSGSGSGTD FTLTISSLEP EDFAMYYCQQ HNEYPWTFGG GTKLEIK                107

SEQ ID NO: 11           moltype = DNA  length = 585
FEATURE                 Location/Qualifiers
misc_feature            1..585
                        note = Chorismate mutase nucleotide (FIG 1A)
source                  1..585
                        mol_type = other DNA
                        organism = synthetic construct
SEQUENCE: 11
atgcgcttcc tgctcgcctt cgtcttcatg ttggctctcg ccagcgcggc ctcggccacc  60
aataacgcca acaacctgga ggagctgatc gccaacgccc tgccggccaa gtacggccag  120
ctcaaggccc aggtggccgc cctccaggcc aacctcacgg cgcagatcaa cgccgtccag  180
gagtcgctcg ccgcggtggc ggccaacgtg cgctacatca agtcgctcga gcagctgggc  240
aacctgcctg acgcctccac ctgcaccaac ctcgactgcg tccgcgcgcc catcaaccag  300
ctcgacgagc tcctcatgca gctctacgcc acgcgcctct cgttcgccct ccaggccggc  360
tacatcaagt acgccgcggg ccaggacgtg ctggactcca gccgcgagtc ggtggtgctg  420
gccaacgccc gcgcgagcgc cgtcgccaac ggcctgcccg agtacgtggg ccaggtcctc  480
tacggcaact actgcatgct ctacgtctcc aagcgccttc aggtggagac cctcaactcc  540
gagttcaacg ccggcctccc cgtccccgtc cagcacgccg attga                  585

SEQ ID NO: 12           moltype = AA  length = 223
FEATURE                 Location/Qualifiers
REGION                  1..223
                        note = Fusarium solani (FIG3)
source                  1..223
                        mol_type = protein
                        organism = unidentified
SEQUENCE: 12
MTIYVPGAVE LPEANLSFLD WYFREQEKLQ SLIRRFESPD EYPFFPDALQ NPILKPLNYP  60
KILHENNVNV NDKIKKFYTE KFLPAVCPDF GREERGESQE NYGSRARCDI ACLQALSRRI  120
HFGKFVAESK FRSDEEKYIR LIMAEDEREG IAESITNAAV EKKVLERLRL KALTYGKEPS  180
IPDGTEGAAK IDVDAVVSMY KDFIPLTKEV EVEYLMQRLE PSA                    223

SEQ ID NO: 13           moltype = AA  length = 266
FEATURE                 Location/Qualifiers
REGION                  1..266
                        note = Fusarium solani (FIG3)
source                  1..266
                        mol_type = protein
                        organism = unidentified
SEQUENCE: 13
MDTVINMADA AHALDLARIR FQLIRLEDTI TFHLIERVQF ALNGTIYVPG AVELPEANLS  60
FLDWYFREQE KLQSLIRRFE SPDEYPFFPD ALQNPILKPL NYPKILHENN VNVNDKIKKF  120
YTEKFLPAVC PDFGREERGE SQENYGSTAT CDIACLQALS RRIHFGKFVA ESKFRSDEEK  180
YIRLIMAEDR EGIAESITNA AVEKKVLERL RLKALTYGKD PSIPDGTEGA AKIDVDAVVS  240
MYKDFVIPLT KEVEVEYLMQ RLEPSA                                       266

SEQ ID NO: 14           moltype = AA  length = 363
FEATURE                 Location/Qualifiers
source                  1..363
                        mol_type = protein
                        note = Staphylococcus aureus (FIG3)
                        organism = Staphylococcus aureus
SEQUENCE: 14
```

-continued

```
MSNKLESYRS EIVSLNHQIL DLLSKRGELA QKIGEEKLKQ GTRIYDPQRE KEMLNDLIDS  60
NKGPFNDNTI KQLFKEIFKA STDLQKSENE KHLYVSRKLK PEDTIVTFDN GGIIGDGNKS 120
FVFGPCSVES FEQVEAVAKN LHAKGEKFIR GGAFKPRTSP YDFQGLGVEG LKILKQIKDK 180
YDLNVVSEIV NPNDFEVADE YLDVFQIGAR NMQNFELLKE AGRTKKPILL KRGLSATIEE 240
FVYAAEYIAS QGNQNIILCE RGIRTYEKAT RNTLDISAVP ILKQGTHLPV MVDVTHSTGR 300
KDIMLPTAKA ALAVGADGVM AEVHPDPSVA LSDAGQQMDL DEFQAFYDEL KPLSDLYNAK 360
KLK                                                              363

SEQ ID NO: 15          moltype = AA  length = 365
FEATURE                Location/Qualifiers
source                 1..365
                       mol_type = protein
                       note = Pseudomonas aeruginosa (FIG3)
                       organism = Pseudomonas aeruginosa
SEQUENCE: 15
MADQDQLKAL RLRIDSLDEK LLELISERAR CAQDVARVKT QTLGEGEAPV FYRPEREAWV  60
LKHIMQLNKG PLDNEEVARL FPEIMSSCLA LEQPLKVAYL GPEGTFTQAA ALKHFGNAVI 120
STPMAAIDEV FREVAAGAVN FGVVPVENST EGAVNHTLDS FLEHDMVICG EVELPIHHHL 180
LVGETTKIDN ITRIYSHAQS LAQCRKWLDS HYPSVERVAV SSNADAAKRV KSEWNSAAIA 240
GDMAASLYDL SKLHEKIEDR PDNSTRFLII GNQEVPPTGD DKTSIIVSMR NKPGALHELL 300
VPFHNNGIDL TRIETRPSRS GKWTYVFFID FVGHHKEPLI KDVLEKIGQE AVALKVLGSY 360
PKAVL                                                            365
```

The invention claimed is:

1. A method for differentially diagnosing keratitis of a patient with *Acanthamoeba* keratitis, the method comprising: detecting an antigen antibody reaction of an antibody or antigen-binding fragment specific to a chorismate mutase protein for a subject derived biological sample, wherein the chorismate mutase protein consists of an amino acid sequence of SEQ ID NO: 1, wherein the antibody specifically binds to an amino acid sequence site of SEQ ID NO: 2 in the chorismate mutase protein, and wherein the antibody or antigen-binding fragment comprises a heavy chain variable domain (VH) comprising the CDRs as set forth in SEQ ID NOs: 3-5 and a light chain variable domain (VL) comprising the CDRs as set forth in SEQ ID NOs: 7-9, and wherein detection of the antigen antibody reaction in the subject derived biological sample is indicative of the subject having *Acanthamoeba* keratitis.

* * * * *